US00RE50535E

(19) United States
(12) Reissued Patent
Dveksler et al.

(10) Patent Number: US RE50,535 E
(45) Date of Reissued Patent: Aug. 19, 2025

(54) COMPOSITIONS COMPRISING PREGNANCY SPECIFIC GLYCOPROTEINS AND METHODS OF USE THEREOF

(71) Applicants: THE HENRY M. JACKSON FOUNDATION FOR THE ADVANCEMENT OF MILITARY MEDICINE, INC., Bethesda, MD (US); THE UNITED STATES OF AMERICA, AS REPRESENTED BY THE SECRETARY, DEPT OF HEALTH AND HUMAN SERVICES, Bethesda, MD (US)

(72) Inventors: Gabriela Dveksler, Bethesda, MD (US); Harry Malech, Bethesda, MD (US)

(73) Assignees: THE HENRY M. JACKSON FOUNDATION FOR THE ADVANCEMENT OF MILITARY MEDICINE, INC., Bethesda, MD (US); THE UNITED STATES OF AMERICA, AS REPRESENTED BY THE SECRETARY, DEPARTMENT OF HEALTH AND HUMAN SERVICES, Bethesda, MD (US)

(21) Appl. No.: 18/319,314

(22) Filed: May 17, 2023

Related U.S. Patent Documents

Reissue of:
(64) Patent No.: 11,007,249
Issued: May 18, 2021
Appl. No.: 15/561,622
PCT Filed: Sep. 16, 2016
PCT No.: PCT/US2016/052131
§ 371 (c)(1),
(2) Date: Sep. 26, 2017
PCT Pub. No.: WO2017/049082
PCT Pub. Date: Mar. 23, 2017

U.S. Applications:
(60) Provisional application No. 62/219,900, filed on Sep. 17, 2015.

(51) Int. Cl.
*A61K 38/17* (2006.01)
*A61P 37/06* (2006.01)

(52) U.S. Cl.
CPC ..... *A61K 38/1774* (2013.01); *A61P 37/06* (2018.01)

(58) Field of Classification Search
CPC ..... A61P 37/06; A61K 38/1774
See application file for complete search history.

(56) References Cited

U.S. PATENT DOCUMENTS

2012/0177645 A1 7/2012 Langermann et al.

FOREIGN PATENT DOCUMENTS

WO 90/07937 A1 7/1990
WO WO2004032867 * 4/2004

OTHER PUBLICATIONS

Blois et al. Mucosal Immunol. Mar. 2014; 7(2): 348-358. (Year: 2014).*
Sara Snyder, "Human Pregnancy-Specific Glycoproteins Function as Immunomodulators in vitro by Inducing 1 secretion of IL-10 and IL-6 in Human Monocytes", 2000, Uniformed Services University of the Health Sciences, Dissertation or Doctor of Philosophy; pp. 1-160.
Shane Thomas (Authorized officer), International Search Report dated Feb. 22, 2017 issued in corresponding International Patent Application No. PCT/US2016/052131, 5 pages.
Carli et al., "Roles of Transforming Growth Factor-β in Graft-versus-Host and Graft-versus-Tumor Effects", Biology of Blood and Marrow Transplantation, 2012, vol. 18, Issue 9, pp. 1329-1340.
Kumar et al., "Prophylaxis of graft-versus-host disease with cyclosporine-prednisone is associated with increased risk of chronic graft-versus-host disease", Bone Marrow Transplantation 2001, vol. 27, pp. 1133-1140.
Sharma et al. (GvHD is attenuated by administration of pregnancy specific protein 1 (PSG1) through induction of immune tolerance; Abstract: National Institutes of Health Research Festival Poster Session III; Sep. 17, 18).*
Carli et al. (Biol Blood Marrow Transplant 18: 1329-1340 (2012)).*
Kumar et al. ("Prophylaxis of graft-versus-host disease with cyclosporine-prednisone is associated with increased risk of chronic graft-versus-host disease" Bone Marrow Transplantation 27, 1133-1140(2001)).*
Sara Snyder, "Human Pregnancy-Specific Glycoproteins Function as Immunomodulators in vitro by Inducing secretion of IL-10 and IL-6 in Human Monocytes", Uniformed Services University of the Health Sciences, Dissertation for Doctor of Philosophy; abstract (2000).
Internationl Search Report issued in corresponding International Patent Application No. PCT/US2016/052131.

* cited by examiner

*Primary Examiner* — Padmashri Ponnaluri
(74) *Attorney, Agent, or Firm* — MH2 Technology Law Group, LLP

(57) ABSTRACT

The present invention relates to methods of treating a subject suffering from or at risk of suffering from graft versus host disease (GvHD) comprising administering a therapeutically effective amount of at least one of pregnancy specific glycoprotein 1 (PSG1) or PSG9 to a subject in need thereof.

4 Claims, 8 Drawing Sheets

Specification includes a Sequence Listing.

COMPOSITIONS COMPRISING PREGNANCY SPECIFIC GLYCOPROTEINS AND METHODS OF USE THEREOF

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

STATEMENT REGARDING FEDERALLY SPONSORED RESEARCH OR DEVELOPMENT

This invention was made with government support under Grant No. 1R21AI101979 awarded by the National Institutes of Health. The Government has certain rights in the invention.

REFERENCE TO SEQUENCE LISTING

A computer readable [text] *XML* file, entitled ["044508-5059-WO-SequenceListing.txt,"] *HMJ-177-US-RE SL.xml,* created on or about [Sep. 16, 2016 HMJ-177-US-RE_SL] *May 16, 2023* with a file size of about [15 kb] *6,817 bytes* contains the sequence listing for this application and is hereby incorporated by reference in its entirety.

BACKGROUND OF THE INVENTION

Field of the Invention

The present invention relates to methods of treating a subject suffering from or at risk of suffering from graft versus host disease (GvHD) comprising administering a therapeutically effective amount of at least one of pregnancy specific glycoprotein 1 (PSG1) or PSG9, or a respective variant thereof, to a subject in need thereof.

Background of the Invention

Hematopoietic stem cell transplantation is curative for many disorders; however, it can be associated with significant morbidity and mortality, often as a result of graft versus host disease (GvHD). GvHD is an immune mediated reaction in which donor T cells recognize the host antigens as foreign, causing donor T cells to proliferate and attack host tissues. Establishment of a tolerogenic immune environment while preserving immune response to infectious agents is required for bone marrow transplantation and GvHD is a significant obstacle to success.

Pregnancy specific glycoproteins (PSGs) are synthesized by the placenta at the onset of pregnancy and are believed to play a role in maintaining a tolerogenic immune environment to prevent rejection of the fetus by the maternal immune system. One specific PSG protein, PSG1, is of particular note as it has been shown to be involved in pathways devoted to induction of immune tolerance. PSG1 is involved in activation of transforming growth factor-β1 (TGFβ1), a cytokine essential to suppression of inflammatory T-cells and important for differentiation of tolerance inducing $CD4^+CD25^+FoxP3^+$ regulatory T cells (Tregs), a cell population shown to be important in the prevention of GvHD.

PSG9 is another member of the PSG family of proteins. There have been reports that this protein, as well as PSG1, inhibits the platelet-fibrinogen interactions, suggesting an anti-thrombotic action. It has also been reported that PSG9 is upregulated in colorectal cancer.

SUMMARY OF THE INVENTION

The present invention relates to methods of treating a subject suffering from or at risk of suffering from graft versus host disease (GvHD) comprising administering a therapeutically effective amount of at least one of pregnancy specific glycoprotein 1 (PSG1) or PSG9, or a respective variant thereof, to a subject in need thereof.

DETAILED DESCRIPTION OF THE INVENTION

Figure 1B:
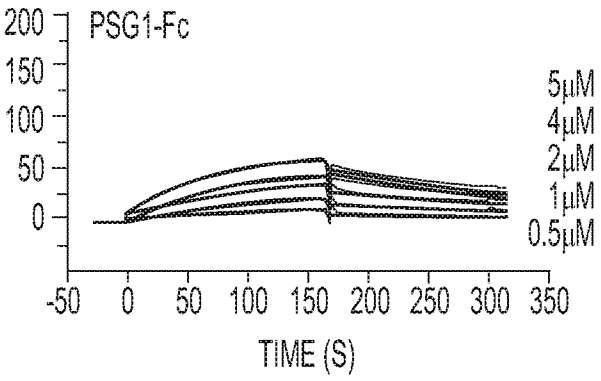
FIG. 1 depicts PSG1 binding directly with the small latent TGF complex (SLC) and latency associated peptide (LAP) of TGFβ1, increasing levels of active TGFβ1. Surface plasmon resonance (SPR) analysis of the interaction of PSG1-Fc with SLC (A) or LAP (B) of TGF-β1. (C) Increasing concentrations of PSG1-GST-B2 or GST were incubated with 50 ng/mL SLC for 1 hr at 37° C. and the % SLC activated was measured with a TGF-βRII-Fc capture ELISA. (D) 2.5 μg/mL of PSG1-GST-B2, or GST were incubated with 50 ng/mL of SLC for 1 hr at 37° C., and then analyzed for active TGF-β1 by ELISA.
Figure 1D:
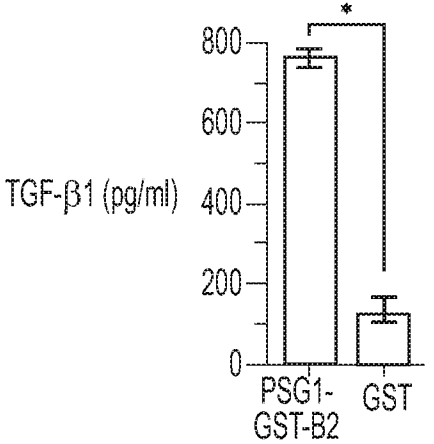
Figure 1A:
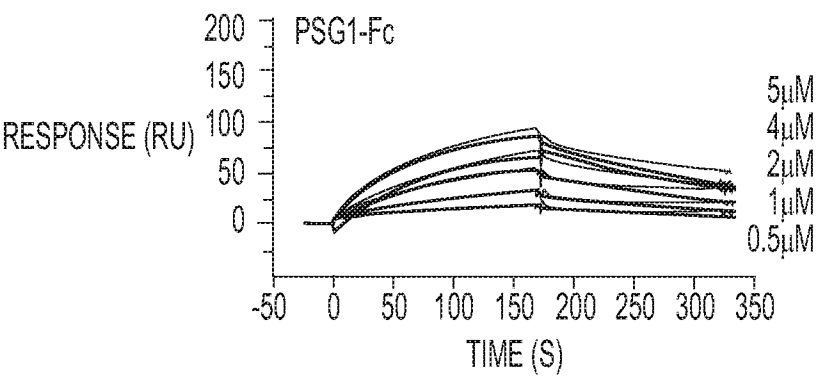
Figure 1C:
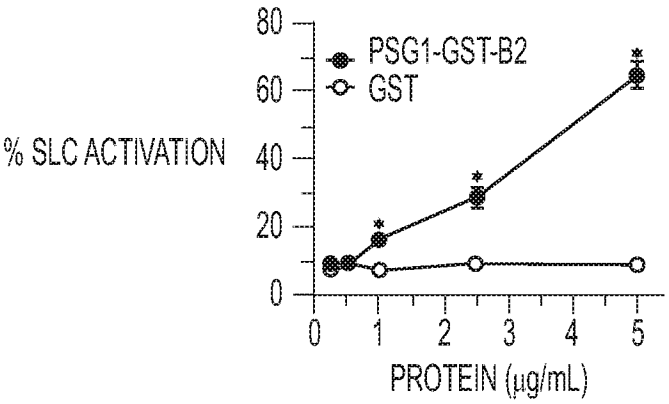
Figure 2A:
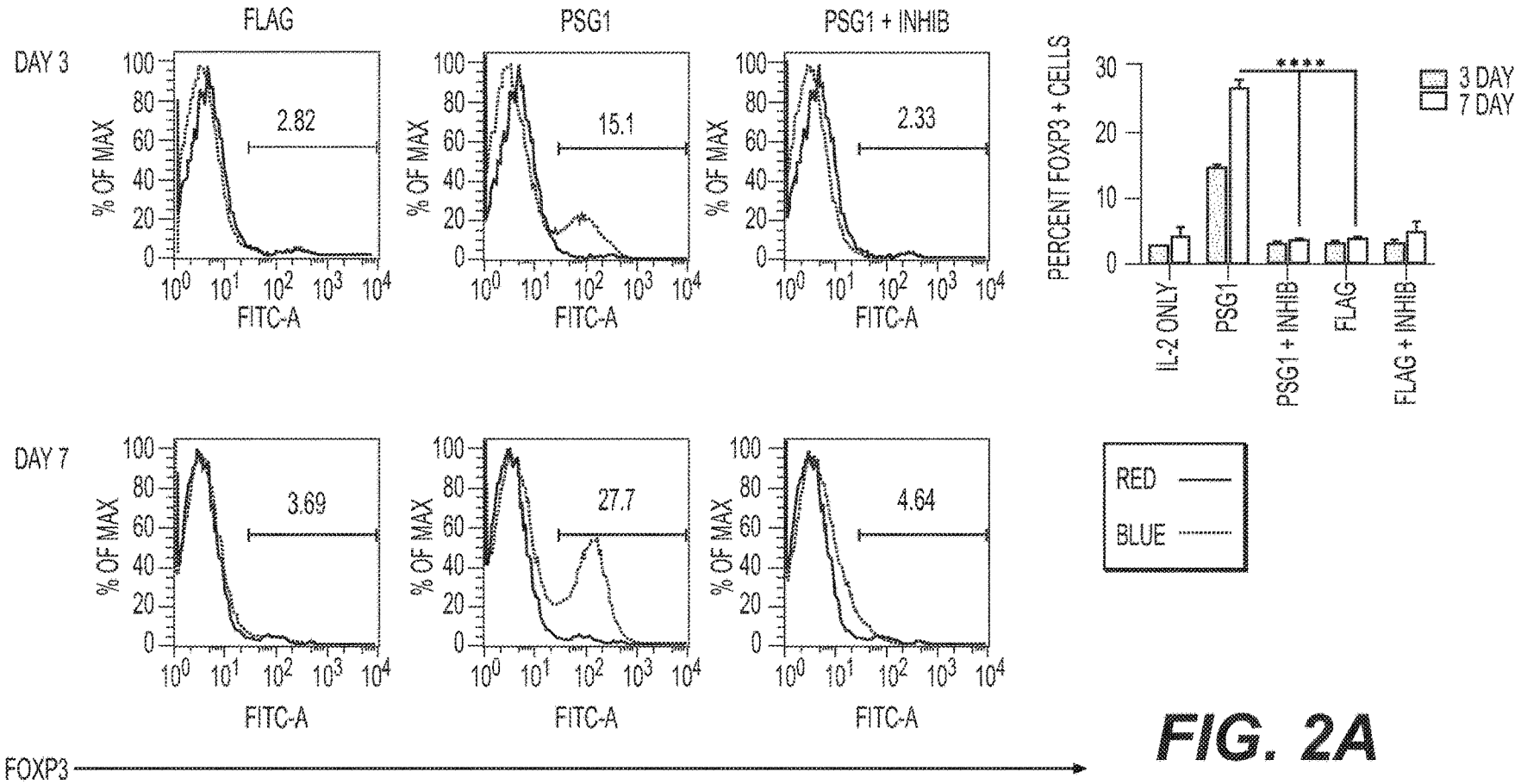
FIG. 2 depicts PSG1 inducing differentiation of Treg cells from naïve mouse and human T-cells in a TGFβ1 dependent manner. (A) T cells were isolated from spleens collected from FoxP3-GFP transgenic mice, a mouse model that expresses GFP in $FoxP3^+$ Treg cells. Cells were stimulated with mouse T-cell activator Dynabeads (anti-CD3/CD28) in the presence of IL-2 (50 ng/ml), IL-2 plus PSG1 (100 ug/ml), IL-2 plus Flag control protein (equimolar concentration) or the previously stated combinations plus the TGFβ receptor I inhibitor SB-431542. Flow cytometry was performed to determine FoxP3 expression (Red=isotype control, Blue=experimental group). (B) T cells were isolated from whole human blood and stimulated as in (A). An additional combination of IL-2 and TGFβ1 (2 ng/ml) was included as a control for FoxP3 expression. All results are gated on CD4+ cells.
Figure 2B:
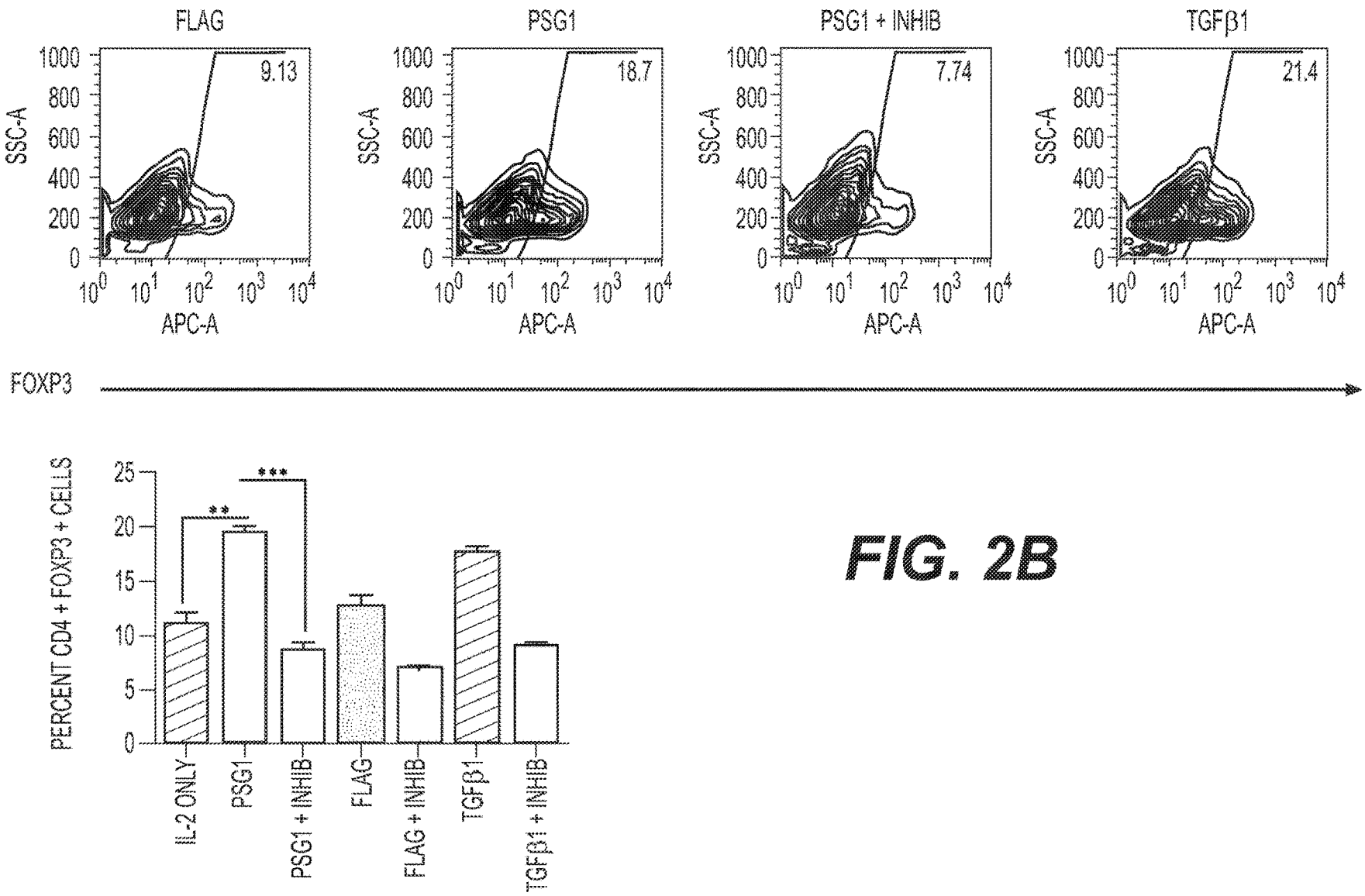
Figure 3:
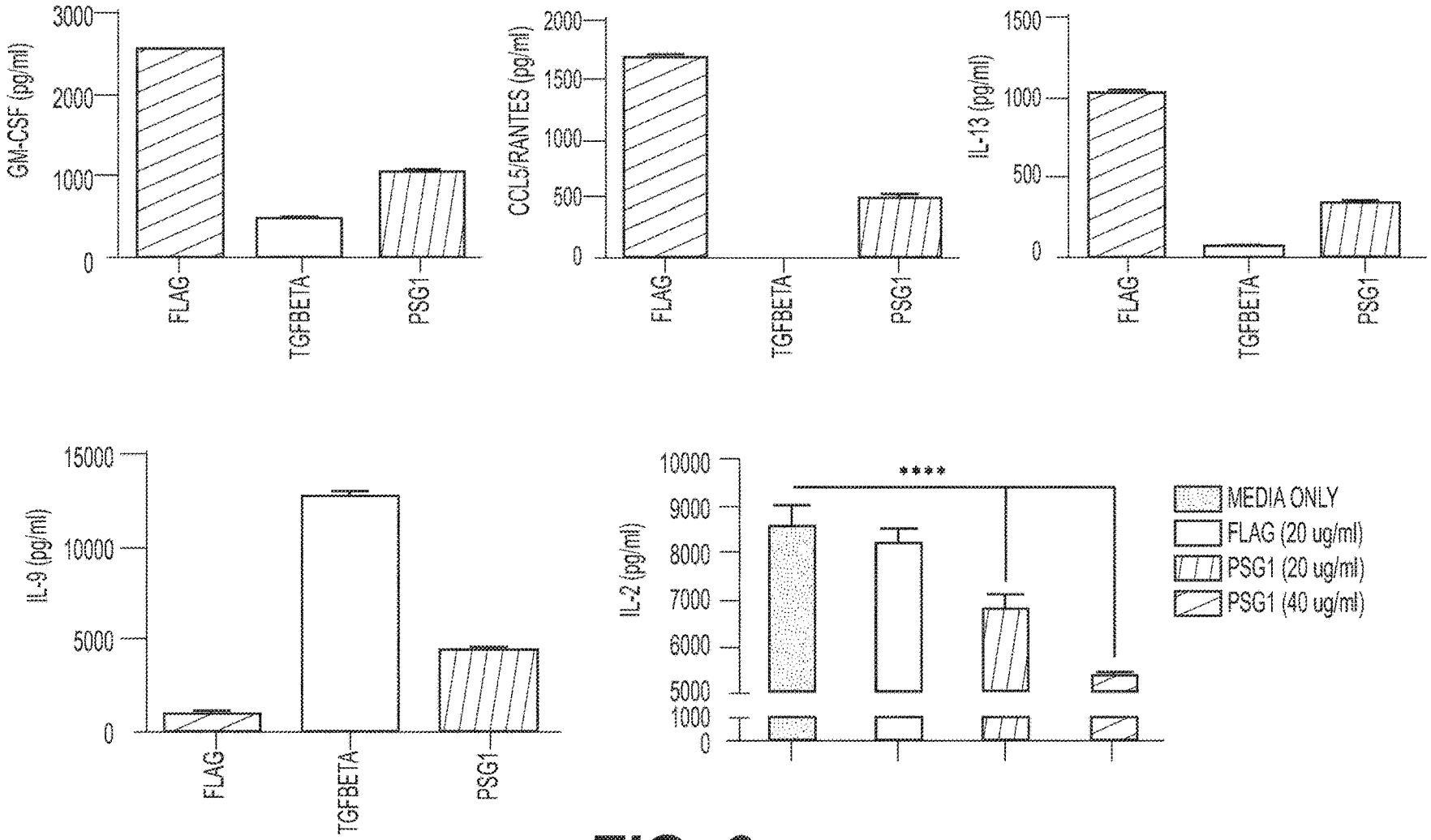
FIG. 3 depicts pro-inflammatory cytokine expression being reduced upon T cell treatment with PSG1, while tolerance inducing cytokine IL-9 is increased. Cells collected from normal B6 mouse spleens were treated with PSG1 (100 ug/ml), TGFβ1 (2 ng/ml) or Flag control protein (equimolar concentration). Pro-inflammatory cytokines GM-CSF, CCLS/RANTES and IL-13 were measured using multiplex immunoassay kits. IL-9, a tolerance inducing cytokine, was increased in cells treated with PSG1. As IL-2 is important for the stability and differentiation of Tregs in vivo and its transcription is suppressed by TGFβ, bioassays were performed on CD4+ naïve T-cells with no added IL-2. In the absence of added IL-2, treatment with PSG1 resulted in an inhibition of IL-2 secretion by activated CD4+ Tcells.
Figure 4:
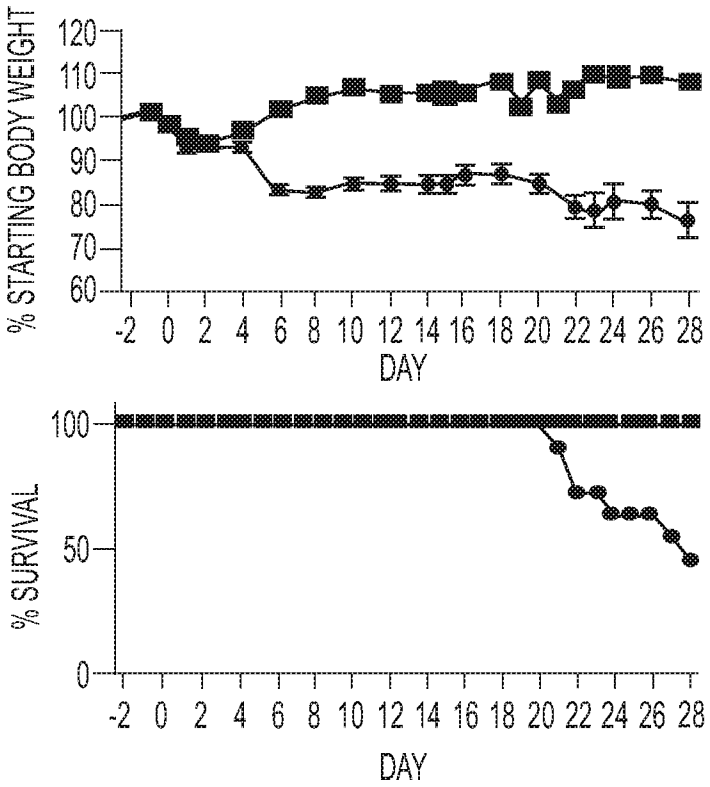
FIG. 4 depicts a mouse model and phenotype of GvHD. Bone marrow cells were collected from the femurs and tibia of 8-9 week old female donors. Total cells were depleted of T cells to yield T-cell depleted bone marrow. Purified T cells were obtained from spleens of donor mice. Two transplant recipient groups were used: genetically matched ($B6D2F_1$/J donors into $B6D2F_1$/J recipients) control mice (BM only) and genetically mismatched (C57BL/6 donors into $B6D2F_1$/J recipients) experimental mice. Transplants were performed by conditioning 8-9 week old female recipients with 850 rads irradiation. Twenty-four hours later, mice were transplanted by lateral tail vein infusion with donor cells. Analysis was performed four weeks after induction. GvHD mice show reduced weight and are scruffy and hunched in appearance, with increased mortality (circle=GvHD mice, square=BM only controls). H/E staining of small intestine (SI) and colon sections from GvHD mice show tissue damage related to inflammation caused by donor T-cells.
Figure 4:
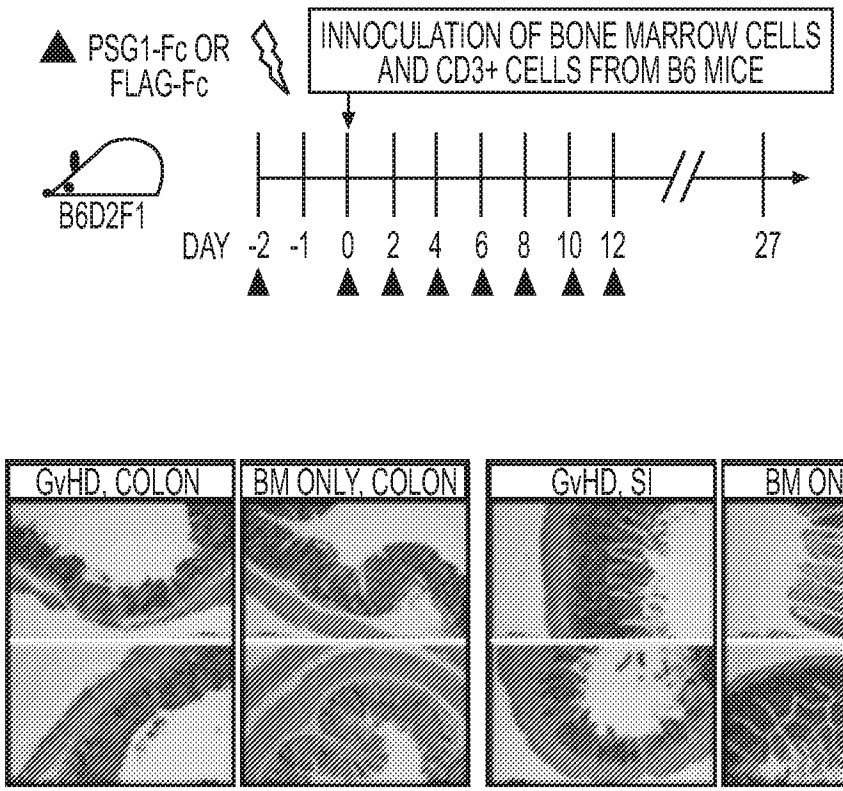
Figure 5A:
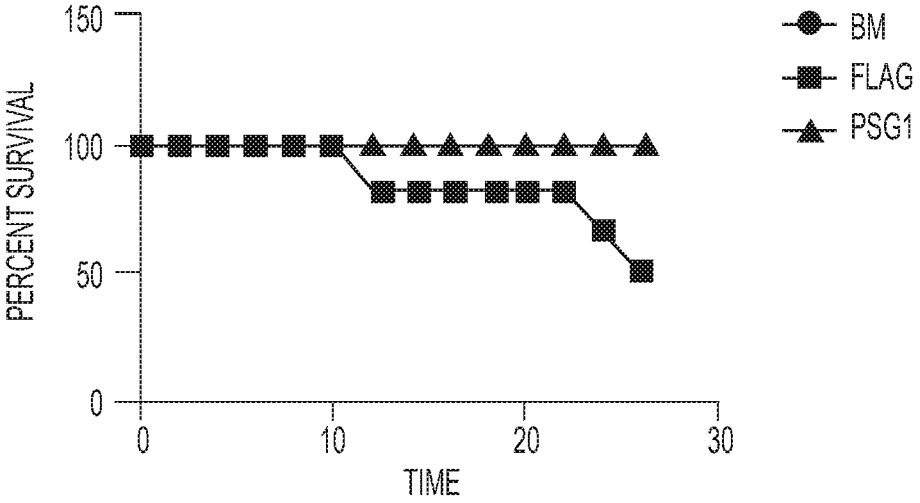
FIG. 5 depicts PSG1 alleviating GvHD in vivo through induction of Treg cells. GvHD mice were treated with 100 μg of PSG1 via I.P. injection every other day for 18 days. Data was collected on day 28 after induction. (A) Survival was improved in mice treated with PSG1. (B) FoxP3 expression was significantly increased in the spleen and increased in the colon after treatment of mice with PSG1. (C) H/E staining of colon shows physiological improvement of mice treated with PSG1. In addition, single positive $CD4^+$ cells (C) and $CD3^+$ cells (D) were reduced in colons of PSG1 treated mice, possibly leading to the reduction in inflammation observed in these tissues.
Figure 5B:
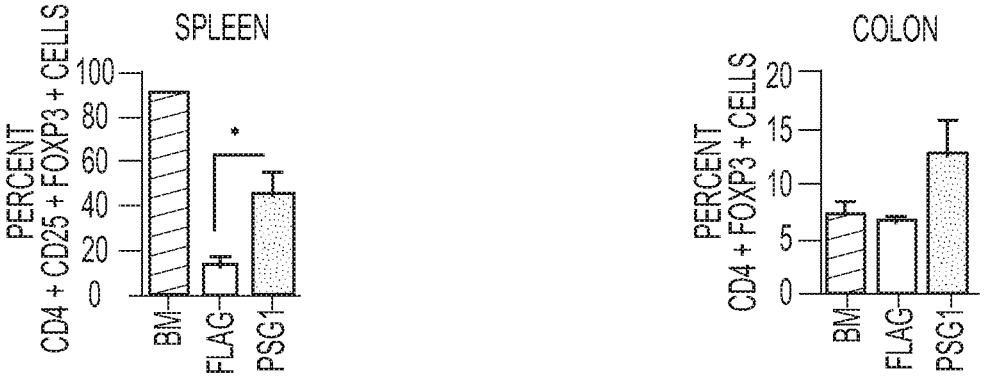
Figure 5C:
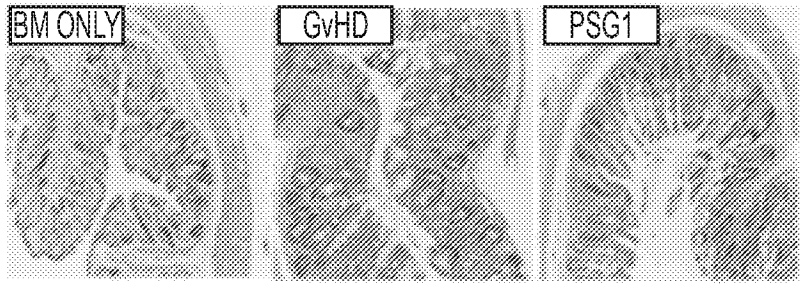
Figure 5C:
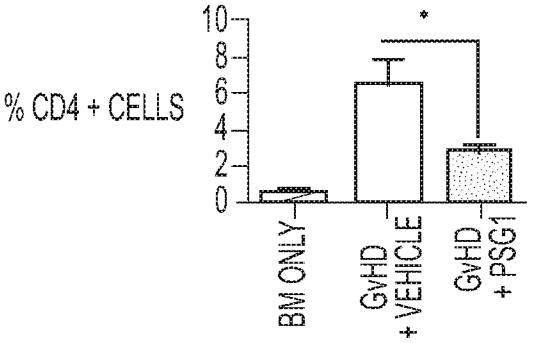
Figure 5D:
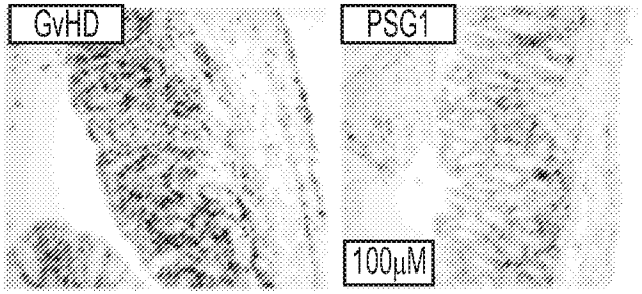
Figure 5D:
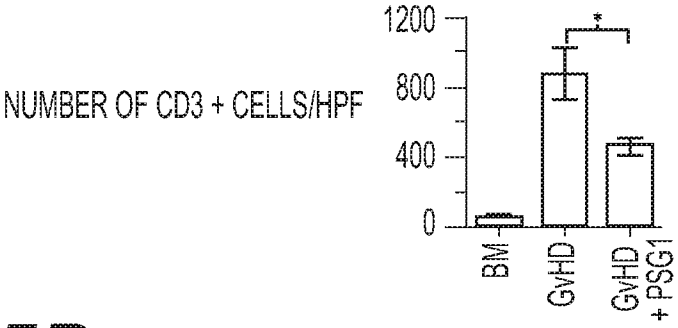
Figure 6:
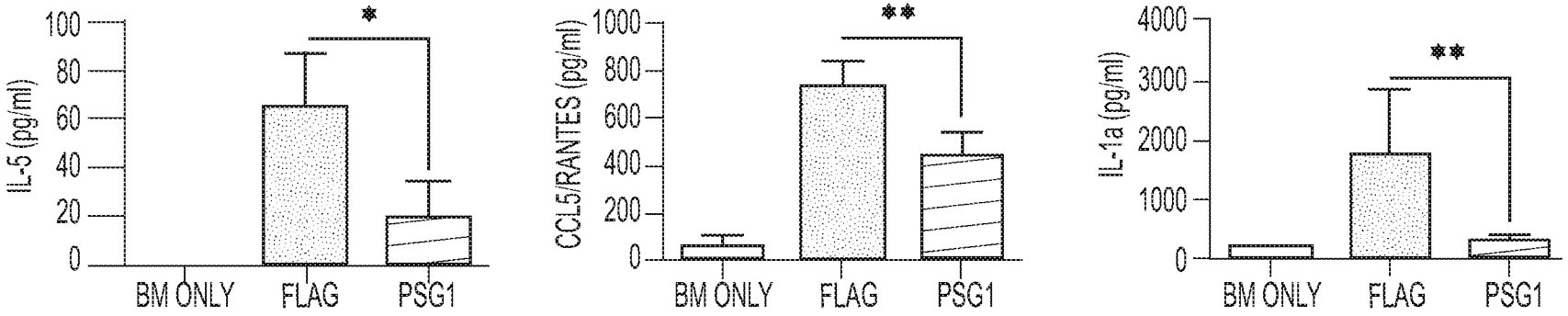
FIG. 6 depicts pro-inflammatory cytokine expression being reduced in GvHD mice treated with PSG1. Blood was collected 26 days after transplant and serum concentrations of pro-inflammatory cytokines IL-5, CCLS/RANTES and IL-1a were measured using multiplex immunoassay kits with the Bioplex system.

A method of treating a subject suffering from or at risk of suffering from graft versus host disease (GvHD) comprising administering a therapeutically effective amount of at least one of a peptide selected from the group consisting of a peptide consisting of the amino acid sequence of SEQ ID NO:2, a peptide comprising an amino acid sequence that is at least 80% identical to the amino acid sequence of SEQ ID NO:2, a peptide consisting of the amino acid sequence of SEQ ID NO:4, and a peptide comprising an amino acid sequence that is at least 80% identical to the amino acid sequence of SEQ ID NO:4.

As used herein, "administering," and "administer" are used to mean introducing at least one compound comprising at least one peptide into a subject. When administration is for the purpose of treatment, the substance is provided at, or after the onset of, a symptom or condition in need of treatment, such as the first symptoms of GvHD. The therapeutic administration of this substance serves to attenuate any symptom, or prevent additional symptoms from arising. When administration is for the purposes of preventing a condition from arising ("prophylactic administration"), the PSG1 and/or PSG9, or a respective variant thereof, are provided in advance of any visible or detectable symptom. The prophylactic administration of the at least one peptide serves to attenuate subsequently arising symptoms or prevent symptoms from arising altogether. The route of administration of the compound includes, but is not limited to, topical, transdermal, intranasal, vaginal, rectal, oral, subcutaneous, intravenous, intraarterial, intramuscular, intraosseous, intraperitoneal, epidural and intrathecal as disclosed herein.

Furthermore, the methods of the present invention would also include coadministering at least two of the peptide of the present invention. The term "coadminister" indicates that each of at least two compounds is administered during a time frame wherein the respective periods of biological activity or effects overlap. Thus the term includes sequential as well as coextensive administration of the any of the compounds of the present invention. And similar to administering compounds, coadministration of more than one substance or the peptides of the present invention can be for therapeutic and/or prophylactic purposes. If more than one substance or peptides of the present invention is coadministered, the routes of administration of the two or more substances need not be the same.

As used herein, "contacting," when used in connection with the methods of the present invention means bringing the at least one of the peptides of the present invention in proximity to the target molecule, tissue or cell such that a specific binding event or a biological effect is possible. Thus, contacting can include adding at least one of the peptides of the present invention in culture medium and applying the culture medium to cells in culture. Contacting also encompasses transfecting a cell with at least one vector described herein and allowing the cell to produce the peptides of the present invention. Of course, contacting would also include administration of the peptides of the present invention, or pharmaceutical compositions thereof, of the present invention to cells in an intact organism. Compositions for administering the peptides of the present invention are described herein.

The treatment methods relate to the administration of glycoproteins. The terms "peptide," "polypeptide," "protein" are used interchangeably herein. It is understood that that a glycoprotein is a protein that has been glycosylated, thus a glycosylated and unglycosylated version of a protein should share the identical amino acid sequence. When discussing proteins, polypeptides or peptides herein, it is understood that the molecules may or may not be glycosylated. As used herein, an "isolated protein" is intended to mean a protein (or glycoprotein) that has been completely or partially removed from its native environment. For example, proteins (or glycoproteins) that have been removed or purified from cells are considered isolated. In addition, recombinantly produced protein (or glycoprotein) molecules contained in host cells are considered isolated for the purposes of the present invention. Moreover, a protein (or glycoprotein) that is found in a cell, tissue or matrix in which it is not normally expressed or found is also considered as "isolated" for the purposes of the present invention. Similarly, proteins (or glycoproteins) that have been synthesized are considered to be isolated proteins (or glycoproteins). "Purified," on the other hand is well understood in the art and generally means that the proteins (or glycoproteins) are substantially free of cellular material, cellular components, chemical precursors or other chemicals beyond, perhaps, buffer or solvent. "Substantially free" is not intended to mean that other components beyond the proteins (or glycoproteins) are undetectable. The proteins (or glycoproteins) of the present invention that are administered may be isolated or purified.

The amino acid sequence of SEQ ID NO:1 represents the full length amino acid sequence of PSG1. The protein is generally formed as propeptide, which usually contains, from N-terminus to C-terminus, a signal sequence and the "mature" peptide. For PSG1 below, the signal sequence occurs from amino acid residues 1-34, and the "mature" peptide is from residues 35-419 of SEQ ID NO:1. The amino acid sequence of hPSG1 is below, is also available within the UniProt Consortium Database as UniProt Accession No. P11464, the entire record of which is incorporated by reference. As used herein, the term "PSG1" can mean the propeptide of PSG1, the mature PSG1, a variant (as defined below) of the propeptide of PSG1 or a variant (as defined below) of the mature PSG1. Any of the various embodiments of PSG1 may or may not be glycosylated.

(SEQ ID NO: 1)

```
MGTLSAPPCT QRIKWKGLLL TASLLNFWNL PTTAQVTIEA
EPTKVSEGKD VLLLVHNLPQ NLTGYIWYKG QMRDLYHYIT
SYVVDGEIII YGPAYSGRET AYSNASLLIQ NVTREDAGSY
TLHIIKGDDG TRGVTGRFTF TLHLETPKPS ISSSNLNPRE
TMEAVSLTCD PETPDASYLW WMNGQSLPMT HSLKLSETNR
TLFLLGVTKY TAGPYECEIR NPVSASRSDP VTLNLLPKLP
KPYITINNLN PRENKDVLNF TCEPKSENYT YIWWLNGQSL
PVSPRVKRPI ENRILILPSV TRNETGPYQC EIRDRYGGIR
SDPVTLNVLY GPDLPRIYPS FTYYRSGEVL YLSCSADSNP
PAQYSWTINE KFQLPGQKLF IRHITTKHSG LYVCSVRNSA
TGKESSKSMT VEVSDWTVP
```

The invention therefore provides methods of using isolated peptides comprising an amino acid sequence at least about 75%, 80%, 85%, 86%, 87%, 88%, 89%, 90%, 91%, 92%, 93%, 94%, 95%, 96%, 97%, 98%, 99% or 100% identical to the amino acid sequence of SEQ ID NO:1. In one specific embodiment, methods comprise the use of a peptide with an amino acid sequence at least 95% identical to the amino acid sequence of SEQ ID NO:1. In further embodiments, the peptides used in the methods of the present invention comprise an amino acid sequence 100% identical to the amino acid sequence of SEQ ID NO:1. In further embodiments, the peptides used in the methods of the present invention consist of an amino acid sequence 100% identical to the amino acid sequence of SEQ ID NO:1.

The amino acid sequence of SEQ ID NO:2, below, represents the mature PSG1 protein without the signal sequence and corresponds to amino acid residues 35-419 of SEQ ID NO:1. The invention therefore provides methods of using peptides comprising an amino acid sequence at least about 75%, 80%, 85%, 86%, 87%, 88%, 89%, 90%, 91%, 92%, 93%, 94%, 95%, 96%, 97%, 98%, 99% or 100% identical to the amino acid sequence of SEQ ID NO:2. In one specific embodiment, the methods utilize peptides with an amino acid sequence at least 95% identical to the amino acid sequence of SEQ ID NO:2. In further embodiments, the peptides used in the methods of the present invention comprise an amino acid sequence 100% identical to the amino acid sequence of SEQ ID NO:2. In further embodiments, the peptides used in the methods of the present invention consist of an amino acid sequence 100% identical to the amino acid sequence of SEQ ID NO:2. A peptide consisting of the amino acid sequence of SEQ ID NO:2 is used to define herein the "wild-type PSG1." Thus, a variant of wild-type PSG1 includes peptides with amino acid sequences comprising the amino acid sequence of SEQ ID NO:2, as well as peptides comprising an amino acid sequence at least about 75%, 80%, 85%, 86%, 87%, 88%, 89%, 90%, 91%, 92%, 93%, 94%, 95%, 96%, 97%, 98%, 99% of the amino acid sequence of SEQ ID NO:2. In one embodiment, the variant of PSG1 does not include a peptide consisting of the amino acid sequence of SEQ ID NO:1.

(SEQ ID NO: 2)

```
QVTIEAEPTK VSEGKDVLLL VHNLPQNLTG YIWYKGQMRD
LYHYITSYVV DGEIIIYGPA YSGRETAYSN ASLLIQNVTR
EDAGSYTLHI IKGDDGTRGV TGRFTFTLHL ETPKPSISSS
NLNPRETMEA VSLTCDPETP DASYLWWMNG QSLPMTHSLK
LSETNRTLFL LGVTKYTAGP YECEIRNPVS ASRSDPVTLN
LLPKLPKPYI TINNLNPREN KDVLNFTCEP KSENYTYIWW
LNGQSLPVSP RVKRPIENRI LILPSVTRNE TGPYQCEIRD
RYGGIRSDPV TLNVLYGPDL PRIYPSFTYY RSGEVLYLSC
SADSNPPAQY SWTINEKFQL PGQKLFIRHI TTKHSGLYVC
SVRNSATGKE SSKSMTVEVS DWTVP
```

The amino acid sequence of SEQ ID NO:3 represents the full length amino acid sequence of PSG9. The protein is generally formed as propeptide, which usually contains, from N-terminus to C-terminus, a signal sequence and the "mature" peptide. For PSG9 below, the signal sequence occurs from amino acid residues 1-34, and the "mature" peptide is from residues 35-4426 of SEQ ID NO:3. The amino acid sequence of hPSG9 is below, is also available within the UniProt Consortium Database as UniProt Accession No. Q00887, the entire record of which is incorporated by reference. As used herein, the term "PSG9" can mean the propeptide of PSG9, the mature PSG9, a variant (as defined below) of the propeptide of PSG9 or a variant (as defined below) of the mature PSG9. Any of the various embodiments of PSG9 may or may not be glycosylated.

(SEQ ID NO: 3)

```
MGPLPAPSCT QRITWKGLLL TASLLNFWNP PTTAEVTIEA
QPPKVSEGKD VLLLVHNLPQ NLPGYFWYKG EMTDLYHYII
SYIVDGKIII YGPAYSGRET VYSNASLLIQ NVTRKDAGTY
TLHIIKRGDE TREEIRHFTF TLYLETPKPY ISSSNLNPRE
AMEAVRLICD PETLDASYLW WMNGQSLPVT HRLQLSKTNR
TLYLFGVTKY IAGPYECEIR NPVSASRSDP VTLNLLPKLP
IPYITINNLN PRENKDVLAF TCEPKSENYT YIWWLNGQSL
PVSPGVKRPI ENRILILPSV TRNETGPYQC EIRDRYGGLR
SNPVILNVLY GPDLPRIYPS FTYYRSGENL DLSCFTESNP
PAEYFWTING KFQQSGQKLF IPQITRNHSG LYACSVHNSA
TGKEISKSMT VKVSGPCHGD LTESQS
```

The invention therefore provides methods of using isolated peptides comprising an amino acid sequence at least about 75%, 80%, 85%, 86%, 87%, 88%, 89%, 90%, 91%, 92%, 93%, 94%, 95%, 96%, 97%, 98%, 99% or 100% identical to the amino acid sequence of SEQ ID NO:3. In one specific embodiment, methods comprise the use of a peptide with an amino acid sequence at least 95% identical to the amino acid sequence of SEQ ID NO:3. In one specific embodiment, the methods utilize peptides with an amino acid sequence at least 95% identical to the amino acid sequence of SEQ ID NO:3. In further embodiments, the peptides used in the methods of the present invention comprise an amino acid sequence 100% identical to the amino acid sequence of SEQ ID NO:3. In further embodiments, the peptides used in the methods of the present invention consist of an amino acid sequence 100% identical to the amino acid sequence of SEQ ID NO:3.

The amino acid sequence of SEQ ID NO:4, below, represents the mature PSG9 protein without the signal sequence and corresponds to amino acid residues 35-426 of SEQ ID NO:1. The invention therefore provides methods of using peptides comprising an amino acid sequence at least about 75%, 80%, 85%, 86%, 87%, 88%, 89%, 90%, 91%, 92%, 93%, 94%, 95%, 96%, 97%, 98%, 99% or 100% identical to the amino acid sequence of SEQ ID NO:4. In one specific embodiment, the methods utilize peptides with an amino acid sequence at least 95% identical to the amino acid sequence of SEQ ID NO:4. In further embodiments, the peptides used in the methods of the present invention comprise an amino acid sequence 100% identical to the amino acid sequence of SEQ ID NO:4. In further embodiments, the peptides used in the methods of the present invention consist of an amino acid sequence 100% identical to the amino acid sequence of SEQ ID NO:4. A peptide consisting of the amino acid sequence of SEQ ID NO:4 is used to define herein the "wild-type PSG9."Thus, a variant of wild-type PSG9 includes peptides with amino acid sequences comprising the amino acid sequence of SEQ ID NO:4, as well as peptides comprising an amino acid sequence at least about 75%, 80%, 85%, 86%, 87%, 88%, 89%, 90%, 91%, 92%, 93%, 94%, 95%, 96%, 97%, 98%, 99% of the amino acid sequence of SEQ ID NO:4. In one embodiment, the variant of PSG9 does not include a peptide consisting of the amino acid sequence of SEQ ID NO:3.

(SEQ ID NO: 4)

```
EVTIEAQPPK VSEGKDVLLL VHNLPQNLPG YFWYKGEMTD

LYHYIISYIV DGKIIIYGPA YSGRETVYSN ASLLIQNVTR

KDAGTYTLHI IKRGDETREE IRHFTFTLYL ETPKPYISSS

NLNPREAMEA VRLICDPETL DASYLWWMNG QSLPVTHRLQ

LSKTNRTLYL FGVTKYIAGP YECEIRNPVS ASRSDPVTLN

LLPKLPIPYI TINNLNPREN KDVLAFTCEP KSENYTYIWW

LNGQSLPVSP GVKRPIENRI LILPSVTRNE TGPYQCEIRD

RYGGLRSNPV ILNVLYGPDL PRIYPSFTYY RSGENLDLSC

FTESNPPAEY FWTINGKFQQ SGQKLFIPQI TRNHSGLYAC

SVHNSATGKE ISKSMTVKVS GPCHGDLTES QS
```

A polypeptide having an amino acid sequence at least, for example, about 95% "identical" to a reference an amino acid sequence, e.g., SEQ ID NO:2, is understood to mean that the amino acid sequence of the polypeptide is identical to the reference sequence except that the amino acid sequence may include up to about five modifications per each 100 amino acids of the reference amino acid sequence. In other words, to obtain a peptide having an amino acid sequence at least about 95% identical to a reference amino acid sequence, up to about 5% of the amino acid residues of the reference sequence may be deleted or substituted with another amino acid or a number of amino acids up to about 5% of the total amino acids in the reference sequence may be inserted into the reference sequence. These modifications of the reference sequence may occur at the N-terminus or C-terminus positions of the reference amino acid sequence or anywhere between those terminal positions, interspersed either individually among amino acids in the reference sequence or in one or more contiguous groups within the reference sequence.

As used herein, "identity" is a measure of the identity of nucleotide sequences or amino acid sequences compared to a reference nucleotide or amino acid sequence. In general, the sequences are aligned so that the highest order match is obtained. "Identity" per se has an art-recognized meaning and can be calculated using published techniques. (See, e.g., Computational Molecular Biology, Lesk, A. M., ed., Oxford University Press, New York (1988); Biocomputing: Informatics And Genome Projects, Smith, D. W., ed., Academic Press, New York (1993); Computer Analysis of Sequence Data, Part I, Griffin, A. M., and Griffin, H. G., eds., Humana Press, New Jersey (1994); von Heinje, G., Sequence Analysis In Molecular Biology, Academic Press (1987); and Sequence Analysis Primer, Gribskov, M. and Devereux, J., eds., M Stockton Press, New York (1991)). While there are several methods to measure identity between two polynucleotide or polypeptide sequences, the term "identity" is well known to skilled artisans (Carillo, H. & Lipton, D., Siam J Applied Math 48:1073 (1988)). Methods commonly employed to determine identity or similarity between two sequences include, but are not limited to, those disclosed in Guide to Huge Computers, Martin J. Bishop, ed., Academic Press, San Diego (1994) and Carillo, H. & Lipton, D., Siam J Applied Math 48:1073 (1988). Computer programs may also contain methods and algorithms that calculate identity and similarity. Examples of computer program methods to determine identity and similarity between two sequences include, but are not limited to, GCG program package (Devereux, J., et al., Nucleic Acids Research 12(i):387 (1984)), BLASTP, ExPASy, BLASTN, FASTA (Atschul, S. F., et al., J Molec Biol 215:403 (1990)) and FASTDB. Examples of methods to determine identity and similarity are discussed in Michaels, G. and Garian, R., Current Protocols in Protein Science, Vol 1, John Wiley & Sons, Inc. (2000), which is incorporated by reference.

In one embodiment of the present invention, the algorithm used to determine identity between two or more polypeptides is BLASTP. In another embodiment of the present invention, the algorithm used to determine identity between two or more polypeptides is FASTDB, which is based upon the algorithm of Brutlag et al. (Comp. App. Biosci. 6:237-245 (1990), incorporated by reference). In a FASTDB sequence alignment, the query and reference sequences are amino sequences. The result of sequence alignment is in percent identity. In one embodiment, parameters that may be used in a FASTDB alignment of amino acid sequences to calculate percent identity include, but are not limited to: Matrix=PAM, k-tuple=2, Mismatch Penalty=1, Joining Penalty=20, Randomization Group Length=0, Cutoff Score=1, Gap Penalty=5, Gap Size Penalty 0.05, Window Size=500 or the length of the subject amino sequence, whichever is shorter.

If the reference sequence is shorter or longer than the query sequence because of N-terminus or C-terminus additions or deletions, but not because of internal additions or deletions, a manual correction can be made, because the FASTDB program does not account for N-terminus and C-terminus truncations or additions of the reference sequence when calculating percent identity. For query sequences truncated at the N- or C-termini, relative to the reference sequence, the percent identity is corrected by calculating the number of residues of the query sequence that are N- and C-terminus to the reference sequence that are not matched/aligned, as a percent of the total bases of the query sequence. The results of the FASTDB sequence alignment determine matching/alignment. The alignment percentage is then subtracted from the percent identity, calculated by the above FASTDB program using the specified parameters, to arrive at a final percent identity score. This corrected score can be used for the purposes of determining how alignments "correspond" to each other, as well as percentage identity. Residues of the reference sequence that extend past the N- or C-termini of the query sequence may be considered for the purposes of manually adjusting the percent identity score. That is, residues that are not matched/aligned with the N- or C-termini of the comparison sequence may be counted when manually adjusting the percent identity score or alignment numbering.

For example, a 90 amino acid residue query sequence is aligned with a 100 residue reference sequence to determine percent identity. The deletion occurs at the N-terminus of the query sequence and therefore, the FASTDB alignment does not show a match/alignment of the first 10 residues at the N-terminus. The 10 unpaired residues represent 10% of the reference sequence (number of residues at the N- and C-termini not matched/total number of residues in the reference sequence) so 10% is subtracted from the percent identity score calculated by the FASTDB program. If the remaining 90 residues were perfectly matched (100% alignment) the final percent identity would be 90% (100% alignment−10% unmatched overhang). In another example, a 90 residue query sequence is compared with a 100 reference sequence, except that the deletions are internal deletions. In this case the percent identity calculated by FASTDB is not manually corrected, since there are no residues at the N- or C-termini of the subject sequence that are not matched/aligned with the query. In still another example, a 110 amino acid query sequence is aligned with a 100 residue reference sequence to determine percent identity. The addition in the query occurs at the N-terminus of the query sequence and therefore, the FASTDB alignment may not show a match/alignment of the first 10 residues at the N-terminus. If the remaining 100 amino acid residues of the query sequence have 95% identity to the entire length of the reference sequence, the N-terminal addition of the query would be ignored and the percent identity of the query to the reference sequence would be 95%.

As used herein, the terms "correspond(s) to" and "corresponding to," as they relate to sequence alignment, are intended to mean enumerated positions within the reference protein, e.g., wild-type PSG1, and those positions in a mutant or related PSG1 that align with the positions on the reference protein. Thus, when the amino acid sequence of a subject peptide is aligned with the amino acid sequence of a reference PSG1, e.g., SEQ ID NO:2, the amino acids in the subject sequence that "correspond to" certain enumerated positions of the reference sequence are those that align with these positions of the reference sequence, e.g., SEQ ID NO:2, but are not necessarily in these exact numerical positions of the reference sequence. Methods for aligning sequences for determining corresponding amino acids between sequences are described herein. Accordingly, the invention provides novel peptides whose sequences correspond to the sequence of SEQ ID NOs:1, 2, 3 or 4.

The invention further embraces other species, preferably mammalian, homologs with amino acid sequences that correspond to the PSG1 or PSG9 the present invention. Species homologs, sometimes referred to as "orthologs," in general, share at least 35%, 40%, 45%, 50%, 60%, 65%, 70%, 75%, 80%, 85%, 90%, 95%, 96%, 97%, 98%, or 99% sequence identity with the human version of the proteins. Such corresponding sequences account for PSG1 or PSG9 protein from across a variety of species, such as canine, feline, mouse, rat, rabbit, monkey, etc. of PSG1 or PSG9.

In another embodiment, the invention provides novel peptides whose sequences correspond to the sequence of SEQ ID NOs:1, 2, 3 or 4 and retain at least some minimal function.

Wild-type PSG1 or wild-type PSG9 with an additional methionine residue at position-1 (Met-1-peptide) are contemplated, as are variants with additional methionine and lysine residues at positions-2 and -1 (Met-2-Lys-1-peptide). Variants of the wild-type PSG 1 or wild-type PSG9 with additional Met, Met-Lys, or Lys residues (or one or more basic residues in general) are particularly useful for enhanced recombinant protein production in bacterial host cells.

Variants resulting from insertion of the polynucleotide encoding the wild-type PSG1 or wild-type PSG9 into an expression vector system are also contemplated. For example, variants (usually insertions) may arise from when the amino terminus and/or the carboxy terminus of wild-type PSG1 or wild-type PSG9 is/are fused to another polypeptide.

In another aspect, the invention provides deletion variants wherein one or more amino acid residues in the wild-type PSG1 or wild-type PSG9 protein are removed. Deletions can be effected at one or both termini of the peptide, or with removal of one or more non-terminal amino acid residues of the peptide. Deletion variants, therefore, include all fragments of the wild-type PSG1 or wild-type PSG9 peptides disclosed herein.

Within the confines of the disclosed percent identity, the invention also relates to substitution variants of the disclosed polypeptides of the invention. Substitution variants include those polypeptides wherein one or more amino acid residues of wild-type PSG1 or wild-type PSG9 are removed and replaced with alternative residues. In one aspect, the substitutions are conservative in nature; however, the invention embraces substitutions that are also non-conservative. Conservative substitutions for this purpose may be defined as set out in the tables below. Amino acids can be classified according to physical properties and contribution to secondary and tertiary protein structure. A conservative substitution is recognized in the art as a substitution of one amino acid for another amino acid that has similar properties. Exemplary conservative substitutions are set out in below.

TABLE I

Conservative Substitutions

| SIDE CHAIN CHARACTERISTIC | AMINO ACID | | | |
|---|---|---|---|---|
| Aliphatic | | | | |
| Non-polar | G | A | P | |
| | I | L | V | |
| Polar - uncharged | C | S | T | M |
| | N | Q | | |
| Polar - charged | D | E | | |
| | K | R | | |
| Aromatic | H | F | W | Y |
| Other | N | Q | D | E |

Alternatively, conservative amino acids can be grouped as described in Lehninger, [Biochemistry, Second Edition; Worth Publishers, Inc. NY, N.Y. (1975), pp. 71 77] as set out below.

TABLE II

| Conservative Substitutions | | | | | |
|---|---|---|---|---|---|
| SIDE CHAIN CHARACTERISTIC | AMINO ACID | | | | |
| Non-polar (hydrophobic) | | | | | |
| A. Aliphatic: | A | L | I | V | P |
| B. Aromatic: | F | W | | | |
| C. Sulfur-containing: | M | | | | |
| D. Borderline: | G | | | | |
| Uncharged-polar | | | | | |
| A. Hydroxyl: | S | T | Y | | |
| B. Amides: | N | Q | | | |
| C. Sylfhydryl: | C | | | | |
| D. Borderline: | G | | | | |
| Positively Charged (Basic): | K | R | H | | |
| Negatively Charged (Acidic) | D | E | | | |

And still other alternative, exemplary conservative substitutions are set out below.

TABLE III

| Conservative Substitutions | |
|---|---|
| Original Residue | Exemplary Substitution |
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu(E) | Asp |
| His (H) | Asn, Gln, Lys, Arg |
| Ile (I) | Leu, Val, Met, Ala, Phe |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr |
| Tyr (Y) | Trp, Phe, Thr, Ser |
| Val (V) | Ile, Leu, Met, Phe, Ala |

It should be understood that the definition of peptides or polypeptides of the invention is intended to include polypeptides bearing modifications other than insertion, deletion, or substitution of amino acid residues. By way of example, the modifications may be covalent in nature, and include for example, chemical bonding with polymers, lipids, other organic and inorganic moieties. Such derivatives may be prepared to increase circulating half-life of a polypeptide, or may be designed to improve the targeting capacity of the polypeptide for desired cells, tissues or organs. Similarly, the invention further embraces PSG1 or PSG9 peptides that have been covalently modified to include one or more water-soluble polymer attachments such as polyethylene glycol, polyoxyethylene glycol or polypropylene glycol.

Chemically modified peptide compositions in which the PSG1 or PSG9 protein is linked to a polymer are included within the scope of the present invention. The polymer may be water soluble to prevent precipitation of the protein in an aqueous environment, such as a physiological environment. Suitable water-soluble polymers may be selected from the group consisting of, for example, polyethylene glycol (PEG), monomethoxypolyethylene glycol, dextran, cellulose, or other carbohydrate based polymers, poly-(N-vinyl pyrrolidone) polyethylene glycol, polypropylene glycol homopolymers, a polypropylene oxide/ethylene oxide copolymer polyoxyethylated polyols (e.g., glycerol) and polyvinyl alcohol. The selected polymer is usually modified to have a single reactive group, such as an active ester for acylation or an aldehyde for alkylation, so that the degree of polymerization may be controlled. Polymers may be of any molecular weight, and may be branched or unbranched, and mixtures of such polymers may also be used. When the chemically modified peptides are destined for therapeutic use, pharmaceutically acceptable polymers may be selected for use.

When the polymer is to be modified by an acylation reaction, the polymer should have a single reactive ester group. Alternatively, if the polymer is to be modified by reductive alkylation, the polymer should have a single reactive aldehyde group. A preferred reactive aldehyde is polyethylene glycol propionaldehyde, which is water stable, or mono Cl—ClO alkoxy or aryloxy derivatives thereof (see U.S. Pat. No. 5,252,714, incorporated by reference herein in its entirety).

Pegylation of PSG1 or PSG9 peptides or variants thereof may be carried out by any of the pegylation reactions known in the art, as described, for example, in the following references: Focus on Growth Factors 3, 4 10 (1992); EP 0 154 316; and EP 0 401 384 (each of which is incorporated by reference herein in its entirety). Preferably, the pegylation is carried out via an acylation reaction or an alkylation reaction with a reactive polyethylene glycol molecule (or an analogous reactive water-soluble polymer). A preferred water-soluble polymer for pegylation of polypeptides is polyethylene glycol (PEG), including, but not limited to bi-functional PEGs. As used herein, "polyethylene glycol" is meant to encompass any of the forms of PEG that have been used to derivatize other proteins, such as mono (Cl—ClO) alkoxy- or aryloxy-polyethylene glycol.

Chemical derivatization of the PSG1 or PSG9 peptides may be performed under any suitable conditions used to react a biologically active substance with an activated polymer molecule. Methods for preparing pegylated peptide will generally comprise the steps of (a) reacting the polypeptide with polyethylene glycol, such as a reactive ester or aldehyde derivative of PEG, under conditions whereby the PSG1 or PSG9 polypeptide becomes attached to one or more PEG groups, and (b) obtaining the reaction products. It will be apparent to one of ordinary skill in the art to select the optimal reaction conditions or the acylation reactions based on known parameters and the desired result.

Pegylated and other polymer modified polypeptides may generally be used to treat conditions that may be alleviated or modulated by administration of the PSG1 or PSG9 polypeptides described herein. The chemically-derivatized PSG1 or PSG9 polypeptide molecules disclosed herein may have additional activities, enhanced or reduced biological activity, or other characteristics, such as increased or decreased half-life, as compared to the nonderivatized molecules. The PSG1 or PSG9 polypeptides, fragments thereof, variants and derivatives, may be employed alone, together, or in combination with other pharmaceutical compositions. For example, cytokines, growth factors, antibiotics, anti-inflammatories and/or chemotherapeutic agents may be co-administered as is appropriate for the indication being treated.

The present invention provides compositions comprising purified polypeptides of the invention. Preferred compositions comprise, in addition to the polypeptide of the invention, a pharmaceutically acceptable (i.e., sterile and non-toxic) liquid, semisolid, or solid diluent that serves as a pharmaceutical vehicle, excipient or medium. Any diluent known in the art may be used. Exemplary diluents include, but are not limited to, water, saline solutions, polyoxyethylene sorbitan monolaurate, magnesium stearate, methyl- and propylhydroxybenzoate, talc, alginates, starches, lactose, sucrose, dextrose, sorbitol, mannitol, glycerol, calcium phosphate, mineral oil and cocoa butter.

The invention also relates to isolated nucleic acids and to constructs comprising these nucleic acids. The nucleic acids of the invention can be DNA or RNA, for example, mRNA. The nucleic acid molecules can be double-stranded or single-stranded; single stranded RNA or DNA can be the coding, or sense, strand or the non-coding, or antisense, strand. In particular, the nucleic acids may encode any peptide of the invention, including, but not limited to variants of PSG1 and/or PSG9. For example, the nucleic acids of the invention include polynucleotide sequences that encode glutathione-S-transferase (GST) fusion protein, poly-histidine (e.g., His6 (*SEQ ID NO:5*)), poly-HN, polylysine, hemagglutinin, HSV-Tag and at least a portion of HIV-Tat. If desired, the nucleotide sequence of the isolated nucleic acid can include additional non-coding sequences such as non-coding 3' and 5' sequences (including regulatory sequences, for example).

Transforming growth factors (TGFs) are pleiotropic cytokines involved in the regulation of many responses of cells of the innate and adaptive immune system, including down regulation of pro-inflammatory cytokine secretion and the expansion of Tregs. Active TGFβ1 is essential to induction of Tregs both in vivo and in vitro and increased levels of TGFβ1 lead to increased expression of FoxP3. TGFβ1, however, must undergo an activation process to mediate its effects. TGFβ1 is translated as a pre-pro-TGF consisting of a signal peptide, the 250 residue Latency Associated Peptide (LAP), and the 110 residue mature TGF peptide. LAP non-covalently wraps around homodimeric mature TGFβ1 to form the small latent TGF-complex (SLC). The latent form of TGFβ1 cannot bind to its receptors and signal until proteolytic cleavage or a conformational change in LAP exposes the mature TGFβ1.

The present invention also relates to methods of activating TGFβ1 comprising contacting latent TGFβ1 with a variant of PSG1 and/or a variant of PSG9. The environment in which the PSG1 variant and/or PSG9 variant is contacted with the latent TGFβ1 can be in vitro, in situ or in vivo. In one embodiment, the methods comprise contacting latent TGFβ1 with a peptide that is a variant of the amino acid sequence of SEQ ID NO:2 or a variant of the amino acid sequence of SEQ ID NO:4. In another embodiment, the methods comprise contacting latent TGFβ1 with a peptide that is a variant of the amino acid sequence of SEQ ID NO:2 and a variant of the amino acid sequence of SEQ ID NO:4.

The present invention also relates to methods of inducing Tregs, i.e., producing induced Tregs (iTregs), comprising contacting T cells with a variant of PSG1 and/or a variant of PSG9. The environment in which the PSG1 variant and/or PSG9 variant is contacted with the T cells can be in vitro, in situ or in vivo. In one embodiment, the methods comprise contacting T cells with a peptide that is a variant of the amino acid sequence of SEQ ID NO:2 or a variant of the amino acid sequence of SEQ ID NO:4. In another embodiment, the methods comprise contacting T cells with a peptide that is a variant of the amino acid sequence of SEQ ID NO:2 and a variant of the amino acid sequence of SEQ ID NO:4.

The compositions, or pharmaceutical compositions, comprising the peptides of the present invention typically comprise the peptide and a pharmaceutically acceptable carrier. As used herein, "pharmaceutically acceptable carrier" or "pharmaceutical carrier" is intended to include any and all solvents, dispersion media, coatings, antibacterial and antifungal agents, isotonic and absorption delaying agents, and the like, compatible with pharmaceutical administration. The nature of the pharmaceutical carrier or other ingredients will depend on the specific route of administration and particular embodiment of the invention to be administered. Examples of techniques and protocols that are useful in this context are, inter alia, found in Remington: The Science and Practice of Pharmacy, Beringer et al. (Eds), 21st Ed., Lippincott Williams & Wilkins (2005), which is incorporated herein by reference in its entirety. Examples of such pharmaceutical carriers or diluents include, but are not limited to, water, saline, Ringer's solution, dextrose solution and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include oral and parenteral (e.g., intravenous, intradermal, subcutaneous, inhalation, transdermal (topical), transmucosal and rectal administration). Solutions or suspensions used for parenteral, intradermal or subcutaneous application can include, but are not limited to, a sterile diluent such as water for injection, saline solution, fixed oils, polyethylene glycols, glycerine, propylene glycol or other synthetic solvents, antibacterial agents such as benzyl alcohol or methyl parabens, antioxidants such as ascorbic acid or sodium bisulfite, chelating agents such as ethylenediaminetetraacetic acid, buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable pharmaceutical carriers include physiological saline, bacteriostatic water, Cremophor ELTM (BASF, Parsippany, N.J.) or phosphate buffered saline (PBS). In all cases, the compositions must be sterile and should be fluid to the extent that easy syringeability exists. It must be stable under the conditions of manufacture and storage and must be preserved against the contaminating action of microorganisms such as bacteria and fungi. The pharmaceutical carrier can be a solvent or dispersion medium containing, for example, water, ethanol, polyol (for example, glycerol, propylene glycol and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it may be desirable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., the PSG peptides and variants thereof) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutical carrier. They can be enclosed in gelatin capsules or compressed into tablets. For the purpose of oral therapeutic administration, the active compound can be incorporated with excipients and used in the form of tablets, troches or capsules. Oral compositions can also be prepared using a fluid pharmaceutical carrier for use as a mouthwash, wherein the compound in the fluid pharmaceutical carrier is applied orally and swished and expectorated or swallowed. Pharmaceutically compatible binding agents, and/or adjuvant materials can be included as part of the composition. The tablets, pills, capsules, troches and the like may contain any of the following ingredients, or compounds of a similar nature, such as but not limited to a binder, such as microcrystalline cellulose, gum tragacanth or gelatin, an excipient such as starch or lactose, a disintegrating agent such as alginic acid, Primogel or corn starch, a lubricant such as magnesium stearate or Sterotes, a glidant such as colloidal silicon dioxide, a sweetening agent such as sucrose or saccharin, or a flavoring agent such as peppermint, methyl salicylate or orange flavoring.

For administration by inhalation, the compounds are delivered in the form of an aerosol spray from pressured container or dispenser which contains a suitable propellant, e.g., a gas such as carbon dioxide or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels or creams as generally known in the art.

In one embodiment, the active compounds are prepared with pharmaceutical carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These compositions can be prepared according to methods known to those skilled in the art, for example, as described in U.S. Pat. No. 4,522,811. It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

EXAMPLES

Using surface plasmon resonance (SPR) analysis, it was shown that PSG1 binds directly to the latency associated peptide (LAP), a protein that confers latency to mature TGFβ1, effectively blocking binding of TGFβ1 to its receptors. Further, bioassays and ELISA data show an increase in the levels of bioactive TGFβ1 after treatment with PSG1, indicating that this protein has a role in TGFβ1 activation through interaction with LAP.

In vitro data using naïve mouse T cells showed that upon treatment with PSG1, there was a significant increase of $CD4^+CD25^+$ cells expressing FoxP3 compared to only 2% in untreated controls. The increase in FoxP3 expression was also observed upon treatment of primary naïve human T-cells with PSG1. When a TGFβ receptor I inhibitor was added to cell culture, this increase in FoxP3 expression was effectively blocked, further indicating that PSG1 induces expression of $FoxP3^+$Tregs through regulation of TGFβ1. As IL-2 is important for the stability and differentiation of Tregs in vivo and its transcription is suppressed by TGFβ, bioassays were performed on $CD4^+$ naïve T cells with no added IL-2. In the absence of added IL-2, treatment with PSG1 resulted in an inhibition of IL-2 secretion by activated $CD4^+$ T cells. Several pro-inflammatory cytokines had reduced expression in cells treated with PSG1 compared to untreated controls, indicating that PSG1 reduced release of cytokines implicated in increased autoimmune response.

Using a murine model of GvHD, mice receiving PSG1 had reduced numbers of infiltrating inflammatory $CD3^+$ T cells in the colon and showed a marked improvement physically and histologically over untreated controls. In addition, PSG1 treated mice had significantly higher expression of FoxP3 in $CD4^+CD25^+$ splenic cells when compared to untreated GvHD controls. Pro-inflammatory cytokines were also reduced in the serum of treated mice.

SEQUENCE LISTING

```
Sequence total quantity: 5
SEQ ID NO: 1            moltype = AA  length = 419
FEATURE                 Location/Qualifiers
```

-continued

```
source                  1..419
                        mol_type = protein
                        organism = Homo sapiens
SEQUENCE: 1
MGTLSAPPCT QRIKWKGLLL TASLLNFWNL PTTAQVTIEA EPTKVSEGKD VLLLVHNLPQ  60
NLTGYIWYKG QMRDLYHYIT SYVVDGEIII YGPAYSGRET AYSNASLLIQ NVTREDAGSY  120
TLHIIKGDDG TRGVTGRFTF TLHLETPKPS ISSSNLNPRE TMEAVSLTCD PETPDASYLW  180
WMNGQSLPMT HSLKLSETNR TLFLLGVTKY TAGPYECEIR NPVSASRSDP VTLNLLPKLP  240
KPYITINNLN PRENKDVLNF TCEPKSENYT YIWWLNGQSL PVSPRVKRPI ENRILILPSV  300
TRNETGPYQC EIRDRYGGIR SDPVTLNVLY GPDLPRIYPS FTYYRSGEVL YLSCSADSNP  360
PAQYSWTINE KFQLPGQKLF IRHITTKHSG LYVCSVRNSA TGKESSKSMT VEVSDWTVP   419

SEQ ID NO: 2            moltype = AA  length = 385
FEATURE                 Location/Qualifiers
source                  1..385
                        mol_type = protein
                        organism = Homo sapiens
SEQUENCE: 2
QVTIEAEPTK VSEGKDVLLL VHNLPQNLTG YIWYKGQMRD LYHYITSYVV DGEIIIYGPA  60
YSGRETAYSN ASLLIQNVTR EDAGSYTLHI IKGDDGTRGV TGRFTFTLHL ETPKPSISSS  120
NLNPRETMEA VSLTCDPETP DASYLWWMNG QSLPMTHSLK LSETNRTLFL LGVTKYTAGP  180
YECEIRNPVS ASRSDPVTLN LLPKLPKPYI TINNLNPREN KDVLNFTCEP KSENYTYIWW  240
LNGQSLPVSP RVKRPIENRI LILPSVTRNE TGPYQCEIRD RYGGIRSDPV TLNVLYGPDL  300
PRIYPSFTYY RSGEVLYLSC SADSNPPAQY SWTINEKFQL PGQKLFIRHI TTKHSGLYVC  360
SVRNSATGKE SSKSMTVEVS DWTVP                                        385

SEQ ID NO: 3            moltype = AA  length = 426
FEATURE                 Location/Qualifiers
source                  1..426
                        mol_type = protein
                        organism = Homo sapiens
SEQUENCE: 3
MGPLPAPSCT QRITWKGLLL TASLLNFWNP PTTAEVTIEA QPPKVSEGKD VLLLVHNLPQ  60
NLPGYFWYKG EMTDLYHYII SYIVDGKIII YGPAYSGRET VYSNASLLIQ NVTRKDAGTY  120
TLHIIKRGDE TREEIRHFTF TLYLETPKPY ISSSNLNPRE AMEAVRLICD PETLDASYLW  180
WMNGQSLPVT HRLQLSKTNR TLYLFGVTKY IAGPYECEIR NPVSASRSDP VTLNLLPKLP  240
IPYITINNLN PRENKDVLAF TCEPKSENYT YIWWLNGQSL PVSPGVKRPI ENRILILPSV  300
TRNETGPYQC EIRDRYGGLR SNPVILNVLY GPDLPRIYPS FTYYRSGENL DLSCFTESNP  360
PAEYFWTING KFQQSGQKLF IPQITRNHSG LYACSVHNSA TGKEISKSMT VKVSGPCHGD  420
LTESQS                                                             426

SEQ ID NO: 4            moltype = AA  length = 392
FEATURE                 Location/Qualifiers
source                  1..392
                        mol_type = protein
                        organism = Homo sapiens
SEQUENCE: 4
EVTIEAQPPK VSEGKDVLLL VHNLPQNLPG YFWYKGEMTD LYHYIISYIV DGKIIIYGPA  60
YSGRETVYSN ASLLIQNVTR KDAGTYTLHI IKRGDETREE IRHFTFTLYL ETPKPYISSS  120
NLNPREAMEA VRLICDPETL DASYLWWMNG QSLPVTHRLQ LSKTNRTLYL FGVTKYIAGP  180
YECEIRNPVS ASRSDPVTLN LLPKLPIPYI TINNLNPREN KDVLAFTCEP KSENYTYIWW  240
LNGQSLPVSP GVKRPIENRI LILPSVTRNE TGPYQCEIRD RYGGLRSNPV ILNVLYGPDL  300
PRIYPSFTYY RSGENLDLSC FTESNPPAEY FWTINGKFQQ SGQKLFIPQI TRNHSGLYAC  360
SVHNSATGKE ISKSMTVKVS GPCHGDLTES QS                                392

SEQ ID NO: 5            moltype = AA  length = 6
FEATURE                 Location/Qualifiers
source                  1..6
                        mol_type = protein
                        organism = synthetic construct
SEQUENCE: 5
HHHHHH                                                             6
```

What is claimed is:

1. A method of treating a [human] *mammalian* subject suffering from graft versus host disease (GvHD) comprising administering to the [human] *mammalian* subject a therapeutically effective amount of at least one peptide selected from the group consisting of:

(a) a peptide comprising the amino acid sequence of SEQ ID NO: 2, and (b) a peptide comprising the amino acid sequence of SEQ ID NO: 4.

2. The method of claim 1, wherein the at least one peptide is a peptide consisting of the amino acid sequence of SEQ ID NO:2.

3. The method of claim 1, wherein the at least one peptide is a peptide consisting of the amino acid sequence of SEQ ID NO:4.

4. The method of claim 1, wherein the route of administration of the peptide is intravascular injection, intraperitoneal injection, intramuscular injection, nasal administration or oral administration.

* * * * *